(12) United States Patent
Girten et al.

(10) Patent No.: US 6,284,735 B1
(45) Date of Patent: Sep. 4, 2001

(54) HP-3228 AND RELATED PEPTIDES TO TREAT SEXUAL DYSFUNCTION

(75) Inventors: Beverly E. Girten, Sunnyvale; Ronald R. Tuttle, Escondido, both of CA (US)

(73) Assignee: Lion Bioscience AG (DE)

(*) Notice: Subject to any disclaimer, the term of this patent is extended or adjusted under 35 U.S.C. 154(b) by 0 days.

(21) Appl. No.: 09/356,386

(22) Filed: Jul. 16, 1999

Related U.S. Application Data

(63) Continuation-in-part of application No. 09/306,686, filed on May 6, 1999, which is a continuation of application No. 09/301,391, filed on Apr. 28, 1999, now Pat. No. 6,127,381.
(60) Provisional application No. 60/083,368, filed on Apr. 28, 1998.

(51) Int. Cl.$^7$ .......................... A61K 38/06; A61K 38/07; A61K 38/03

(52) U.S. Cl. ................. 514/16; 514/17; 514/18; 530/329; 530/330; 530/331

(58) Field of Search ................. 514/17, 18, 16; 530/306, 312, 329, 330, 331

(56) References Cited

U.S. PATENT DOCUMENTS

| | | | |
|---|---|---|---|
| 5,010,175 | 4/1991 | Rutter et al. | 530/334 |
| 5,182,366 | 1/1993 | Huebner et al. | 530/334 |
| 5,288,514 | 2/1994 | Ellman | 427/2 |
| 5,324,483 | 6/1994 | Cody et al. | 422/131 |
| 5,420,109 | 5/1995 | Suto et al. | 514/8 |
| 5,439,938 | * 8/1995 | Snyder et al. | 514/565 |
| 5,618,791 | 4/1997 | Yu-Cang Du | 514/17 |
| 5,726,156 | 3/1998 | Girten et al. | 514/16 |
| 5,837,521 | 11/1998 | Cone et al. | 435/204.1 |
| 5,874,443 | 2/1999 | Kiely et al. | 514/309 |
| 5,889,056 | * 3/1999 | Hodson et al. | 514/562 |
| 5,916,899 | 6/1999 | Kiely et al. | 514/309 |
| 6,051,555 | * 4/2000 | Hadley | 514/11 |
| 6,054,556 | 4/2000 | Huby et al. | 530/317 |
| 6,100,048 | 8/2000 | Cone et al. | 435/7.21 |
| 6,127,381 | * 10/2000 | Basu et al. | 514/307 |

FOREIGN PATENT DOCUMENTS

| | | |
|---|---|---|
| 0 590 455 | 9/1993 | (EP) . |
| WO 91/19735 | 12/1991 | (WO) . |
| WO 94/01102 | 1/1994 | (WO) . |
| WO 95/02566 | 1/1995 | (WO) . |
| WO 95/04277 | 2/1995 | (WO) . |
| WO 95/13086 | 5/1995 | (WO) . |
| WO 96/27386 | 9/1996 | (WO) . |
| WO 97/22356 | 6/1997 | (WO) . |

OTHER PUBLICATIONS

Abou–Mohamed et al., "HP–228, a novel synthetic peptide, inhibits the induction of nitric oxide synthase in vivo but not in vitro," *J. Pharmacology Experimental Therapeutics*, 275:584–591 (1995).

Berge et al., "Pharmaceutical salts," *J. Pharm. Sci.*, 66:1–19 (1977).

Castagnoli, "The condensation of succinic anhydride with benzylidinemethylamine. A stereoselective synthesis of trans– and cis–1–Methyl–4–carboxy–5–phenyl–2–pyrrolidinone." *J. of Org. Chem.*, 34(10):3187–3189 (1969).

Catania and Lipton, "α–Melanocyte–Stimulating Hormone Peptides in Host Response, From Basic Evidence to Human Research," *Annals N.Y. Acad. Sci.*, 680:412–423 (1993).

Catania et al., "The Neuropeptide α–MSH Has Specific Receptors on Neutrophils and Reduces Chemotaxis In Vitro," *Peptides*, 17(4):675–679 (1996).

Chowdhary et al., "Localization of the human melanocortin–5 receptor gene (MC5R) to chromosome band 18p11.2 by fluorescence in situ hybridization," *Cytogenet. Cell Genet.* 68:79–81 (1995).

Coppola, Gary, "Novel heterocycles. 8. Fused isoquinolines derived from the reaction of homophthalic anhydride with cyclic imino ethers." *J. Heterocyclic Chem.*, 18:767–770 (1981).

Cushman and Castagnoli, "The synthesis of trans–3–methylnicotine." *J. Org. Chem.*, 37(8):1268–1271 (1972).

Cushman and Castagnoli, "Synthesis of pharmacologically active nitrogen analogs of the tetrahydrocannabinols." *J. Org. Chem.*, 39(11):1546–1550 (1974).

Cushman and Castagnoli, "The condensation of succinic anhydrides with schiff bases. Scope and mechanism." *J. Org. Chem.*, 36(22):3404–3406 (1971).

Cushman and Castagnoli, "A novel approach to the synthesis of nitrogen analogs of the tetrahydrocannabinols." *J. Org. Chem.*, 38(3):440–448 (1973).

Cushman and Madaj, "A study and mechanistic interpretation of the electronic and steric effects that determine the stereochemical outcome of the reaction of schiff bases with homophthalic anhydride and a 3–phenylsuccinic anhydride." *J. Org. Chem.*, 52(5):907–915 (1987).

Dooley et al., "Melanocortin receptor binding assay in rat brain homogenate: identification of tetrapeptide ligands from a combinatorial library," *Society for Neuroscience* 23:964 Abstract 383.18 (Aug. 21, 1997).

Dorr et al., "Evaluation of melanotan–II, a superpotent cyclic melanotropic peptide in a pilot phase–I clinical study," *Life Sci.*, 58(20):1777–1784 (1996).

Fan et al., "Role of melanocortinergic neurons in feeding and the agouti obesity syndrome," *Nature*, 385:165–168 (1997).

(List continued on next page.)

Primary Examiner—Jeffrey E. Russel
(74) Attorney, Agent, or Firm—Campbell & Flores LLP

(57) ABSTRACT

Methods for treating erectile dysfunction in males and sexual dysfunction, such as sexual arousal disorder, in females. The methods involve administering an effective dose of certain compounds, such as HP–228, having the generic formula $$X_1-X'_2-(D)Phe-Arg-(D)Trp-X_3.$$

33 Claims, No Drawings

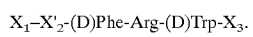

OTHER PUBLICATIONS

Frandberg et al., "Glutamine$^{235}$ and arginine$^{272}$ in human melanocortin 5 receptor determines its low affinity to MSH," *Biochem. Biophys. Res. Commun.* 236:489–492 (1997).

Friedman, "The alphabet of weight control," *Nature*, 385:119–120 (1997).

Gallop et al., "Applications of Combinatorial Technologies to Drug Discovery. 1. Background and Peptide Combinatorial Libraries," *J. Med. Chem.*, 37:1233–1251 (1994).

Gantz et al., "Molecular cloning, expression, and gene localization of a fourth melancortin receptor," *J. Biol. Chem.* 268:15174–15179 (1993).

Gantz et al., "Molecular cloning of a novel melanocortin receptor," *J. Biol. Chem.* 268:8246–8250 (1993).

Gantz et al., "Molecular cloning, expression, and characterization of a fifth melanocortin receptor," *Biochem. Biophys. Res. Commun.* 200:1214–1220 (1994).

Goff and Zuckermann, "Solid–phase synthesis of highly substituted peptide 1(2H)–Isoquinolinones." *J. Org. Chem.*, 60:5748–5749 (1995).

Gordon et al., "Application of combinatorial technologies to drug discovery. 2. Combinatorial organic synthesis, library screening strategies, and future directions." *J. of Med. Chem.*, 37(10):1385–1401 (1994).

Gura, "Obesity Sheds Its Secrets," *Science*, 275:751–753 (1997).

Haimova et al., "A highly stereoselective synthesis of 3,4–dihydro–1(2H)–isoquinolinones and 8–oxoberbines from homophthalic anhydrides and azomethines." *Tetrahedron*, 33:331–336 (1977).

Haskell–Luevano et al., "Binding and cAMP studies of melanotropin peptides with the cloned human peripheral melanocrotin receptor, hMC1R," *Biochem. Biophys. Res. Commun.* 204:1137–1142 (1994).

Haskell–Luevano et al., "Discovery of prototype peptidomimetic agonists at the human melanocortin receptors MC1R and MC4R," *J. Med. Chem.* 40:2133–2139 (1997).

Hotamisligil and Spiegelman, "Tumor necrosis factor α: A key component of the obesity–diabetes link," *Diabetes*, 43:1271–1278 (1994).

Hotamisligil et al., "Reduced tyrosine kinase activity of the insulin receptor in obesity–diabetes. Central role of tumor necrosis factor–alpha," *J. Clin. Invest.*, 94:1543–1549 (1994).

Hotamisligil et al., "Increased adipose tissue expression of tumor necrosis factor–alpha in human obesity and insulin resistance," *J. Clin. Invest.*, 95:2409–2415 (1995).

Houghten et al., "Generation and use of synthetic peptide combinatorial libraries for basic research and drug discovery." *Nature*, 354:84–86 (1991).

Huszar et al., "Targeted disruption of the melanocortin–4 receptor results in obesity in mice," *Cell*, 88:131–141 (1997).

Lee et al., Cycloaddition of Homophthalic Anhydrides to Azodicarboxylate and Alkylidenecarbamates. *Chemical Abstracts*, 106(3):18331a (1987).

Ollman et al., "Antagonism of central melanocortin receptors in vitro and in vivo by agouti–related protein," *Science*, 278:135–138 (1997).

Omholt et al., "Oral Formulation of the Heptapeptide HP 228 Modulates Inflammation and Resting Oxygen Consumption in the Mouse and Rat," *The Pharmacologist*, 39(1):29, Abstract 53 (1997).

Ostresh et al., "Libraries from libraries: Chemical transformation of combinatorial libraries to extend the range and repertoire of chemical diversity." *Proc. Natl. Acad. Sci. USA*, 91:11138–11142 (1994).

Platzer et al., "Up–regulation of monocytic IL–10 by tumor necrosis factor–α and cAMP elevating drugs," *International Immunology*, 7(4)517–523 (1995).

Schiöth et al., "Characterization of the binding of MSH–B, HP–228, GHRP–6 and 153N–6 to the human melanocortin receptor subtypes," *Neuropeptides* 31:565–571 (1997).

Smith et al., "Synthetic approaches to hexahydropyrrolo [1,2-b] isoquinolinones," *J. Heterocyclic Chem.*, 26:1815–1817 (1989).

Smith and Atigadda, "Condensation of homophthalic anhydrides with heterocyclic imines and DMAD under mild conditions," *J. Heterocyclic Chem.*, 28:1813–1815 (1991).

Star et al., "Evidence of autocrine modulation of macrophage nitric oxide synthase by α–melanocyte–stimulating hormone," *Proc. Natl. Acad. Sci. USA*, 92:8016–8020 (1995).

Tamura et al., "Strong base induced cycloaddition of homophthalic anhydrides leading to peri–hydroxy polycyclic compounds." *J. Org. Chem.*, 49:473–478 (1984).

Tamura et al., "Cycloaddition of homophthalic anhydride: A new and simple route to linearly condensed phenolic compounds." *Tetrahedron Letters*, 22(43):4283–4286 (1981).

Tatro, "Receptor biology of the melanocortins, a family of neuroimmunomodulatory peptides," *Neuroimmunomodulation*, 3:259–284 (1996).

Vergoni et al., "Differential influence of a selective melanocortin MC4 receptor antagonist (HS014) on melanocortin–induced behavioral effects in rats," *Eur. J. Pharmacol.*, 362:95–101 (1998).

Wenker, Henry, "Syntheses from ethanolamine. V. Synthesis of Δ–Oxazoline and of 2,2'–Δ$^2$–Di–oxazoline." *J. of Am. Chem. Society*, 60(8):2152–2153 (1938).

Xia et al., "Expression of melanocortin 1 receptor in periaqueductal gray matter," *Neuroreport*, 6:2193–2196 (1995).

Abou–Mohammed et al., "HP–228, A Novel Synthetic Peptide, Inhibits the Induction of Nitric Oxide Synthase In Vivo But not In Vitro," *J. Pharmacol. Experimental Ther.*, 275:584–591 (1995).

\* cited by examiner

HP-3228 AND RELATED PEPTIDES TO TREAT SEXUAL DYSFUNCTION

This application is a continuation-in-part of U.S. application Ser. No. 09/306,686, filed May 6, 1999, which is a continuation of U.S. application Ser. No. 09/301,391, filed Apr. 28, 1999, now U.S. Pat. No. 6,127,381, which claims benefit of U.S. Provisional Application No. 60/083,368, filed Apr. 28, 1998, each of which is incorporated herein by reference. All publications and patents cited herein are also incorporated by reference.

BACKGROUND OF THE INVENTION

1. Field of the Invention

The present invention relates to melanocortin receptors and more specifically to the treatment of sexual dysfunction using melanocortin receptor 3 ligands.

2. Background Information

Sexual dysfunction can be due to several physiological, as well as psychological, factors. In males, erectile dysfunction can be associated with diseases such as diabetes mellitus, syphilis, alcoholism, drug dependency, hypopituitarism and hypothyroidism. Erectile dysfunction can also be caused by vascular and neurogenic disorders, or be a side effect of drugs such as hypertensives, sedatives, tranquilizers and amphetamines. In all, erectile dysfunction is estimated to affect up to 10 million men in the United States, with its incidence increasing with age up to 25% of men at age 65.

While various pharmaceutical treatments are commercially available or being developed, the underlying physiological bases for sexual dysfunction are not well understood. Attention has recently been drawn to melanocortin (MC) receptors, which are a group of cell surface proteins that mediate a variety of physiological effects. The MC receptors have been implicated in the regulation of adrenal gland function such as production of the glucocorticoid cortisol and aldosterone, control of melanocyte growth and pigment production, thermoregulation, immunomodulation and analgesia. Five distinct MC receptors have been cloned, although the specific role of each MC receptor is still unclear.

Certain compounds, termed "melanocortins" have been found to bind MC receptors, causing the activity of the receptors to increase or decrease. These melanocortins include melanocyte-stimulating hormones (MSH) such as α-MSH, β-MSH and γ-MSH, as well as adrenocorticotropic hormone (ACTH). Other compounds may bind as ligands to MC receptors, increasing or decreasing the activity of the receptors.

Thus, there is a need for compounds that can affect the activity of specific MC receptors that are involved with sexual dysfunction. The present invention satisfies this need and provides related advantages as well.

SUMMARY OF THE INVENTION

The present invention provides a method for treating sexual dysfunction, such as erectile dysfunction or sexual arousal disorder, with a compound having the eneric formula $X_1-X_2$-(D)Phe-Arg-(D)Trp-$X_3$. A particularly useful compound is HP-228, which has the formula Ac-Nle-Gln-His-(D)Phe-Arg-(D)Trp-Gly-$NH_2$.

The invention also provides methods for selecting melanocortin receptor-3 ligands by determining whether a compound modulates the activity of MC-3 as an agonist or antagonist. These methods can be used to screen compound libraries for ligands to treat sexual dysfunction and other MC-3-associated conditions.

DETAILED DESCRIPTION OF THE INVENTION

The present invention provides a method for treating sexual dysfunction. The term "sexual dysfunction" herein means any condition that inhibits or impairs normal sexual function, including coitus. However, the term need not be limited to physiological conditions, but may include psychogenic conditions or perceived impairment without a formal diagnosis of pathology.

In males, sexual dysfunction includes erectile dysfunction. The term "erectile dysfunction" or "impotence" means herein the inability or impaired ability to attain or sustain an erection that would be of satisfactory rigidity for coitus. Sexual dysfunction in males can also include premature ejaculation and priapism, which is a condition of prolonged and sometimes painful erection unrelated to sexual activity, often associated with sickle-cell disease.

In females, sexual dysfunction includes sexual arousal disorder. The term "sexual arousal disorder" means herein a persistent or recurrent failure to attain or maintain the lubrication-swelling response of sexual excitement until completion of sexual activity. Sexual dysfunction in females can also include inhibited orgasm and dyspareunia, which is painful or difficult coitus.

The method for treating sexual dysfunction comprises the step of administering to the subject an effective dose of the compound

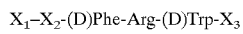

wherein

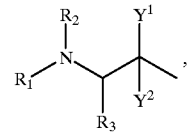

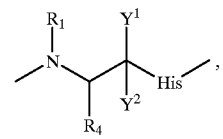

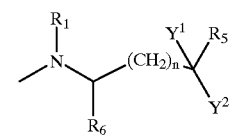

$R_1$ is H, $COCH_3$, $C_2H_5$, $CH_2Ph$, COPh, COO-t-butyl, $COOCH_2Ph$, $CH_2CO$-(polyethylene glycol) or A;

$R_2$ is H, $COCH_3$, $C_2H_5$ or $CH_2Ph$;

$R_3$ is a linear alkyl group having 1 to 6 carbon atoms or a branched or cyclic alkyl group having 3 to 6 carbon atoms;

$R_4$ is $(CH_2)_m-CONH_2$, $(CH_2)_m-CONHR_1$ or $(CH_2)_m-CONHA$;

$R_5$ is OH, $OR_3$, $NH_2$, SH, $NHCH_3$, $NHCH_2Ph$ or A;

$R_6$ is H or $R_3$;

$R_7$ is H, $COCH_3$, $C_2H_5$, $CH_2Ph$, COPh, COO-t-butyl, $COOCH_2Ph$ or $CH_2CO$-(polyethylene glycol);

Ph is $C_6H_5$; m is 1, 2 or 3; n is 0, 1, 2 or 3; $Y^1$ and $Y^2$ are independently hydrogen atoms, or are taken together to form a carbonyl or thiocarbonyl; and A is

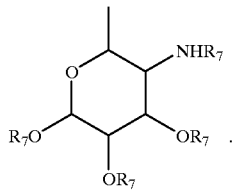

These peptide compounds are characterized in part by the core structures (D)Phe-Arg-(D)Trp or His-(D)Phe-Arg-(D)Trp and are described in U.S. Pat. No. 5,420,109, issued May 30, 1995, and U.S. Pat. No. 5,726,156, issued Mar. 10, 1998.

Particular compounds can be selected by further defining one or more of the individual variables in the generic formula above. The variable $X_1$ can be norleucine or Ac-norleucine; or even norvaline, Ac-norvaline, leucine, Ac-leucine, isoleucine or Ac-isoleucine. The variable $X_2$ can be Gln-His or His. The variable $X_3$ can be Gly or Gly-$NH_2$. The variable $R_1$ can be H, $C_2H_5$ or $CH_2Ph$. The variables $R_1$ and $R_2$ can be $COCH_3$ or H independently. The variable $R_5$ can be $NH_2$. The variable $R_5$ can be covalently bound to $X_1$, forming a cyclic peptide.

A particularly useful compound is HP-228, which has the formula Ac-Nle-Gln-His-(D)Phe-Arg-(D)Trp-Gly-$NH_2$. HP-228 can be synthesized as described in Example I.A. The effectiveness of HP-228 in treating sexual dysfunction such as erectile dysfunction is demonstrated in Example II.

Other useful compounds can have the (D)Phe of the formula be iodinated in the para position. Thus, a useful compound is HP-467, which has the formula Ac-Nle-Gln-His-(para-iodo-(D)Phe)-Arg-(D)Trp-Gly-$NH_2$. HP-467 can be prepared as further described in Example I.B.

Other specific compounds useful in the method of the invention include (D) Phe-Arg-(D)Trp
Ac-(D)Phe-Arg-(D)Trp
(D)Phe-Arg-(D)Trp-$NH_2$
Ac-(D)Phe-Arg-(D)Trp-$NH_2$
(cyclohexyl)Gly-Gln-His-(D)Phe-Arg-(D)Trp-Gly
Ac-(cyclohexyl)Gly-Gln-His-(D)Phe-Arg-(D)Trp-Gly-$NH_2$
cyclo(His-(D)Phe-Arg-(D)Trp)
Nle-Gln-His-(D)Phe-Arg-(D)Trp-Gly-$NH_2$
His-(D)Phe-Arg-(D)Trp-Gly
His-(D)Phe-Arg-(D)Trp-Gly-$NH_2$
Ac-His-(D)Phe-Arg-(D)Trp-$NH_2$
His-(D)Phe-Arg-(D)Trp-OH
His-(D)Phe-Arg-(D)Trp
His-(D)Phe-Arg-(D)Trp-$NH_2$
Ac-His-(D)Phe-Arg-(D)Trp-OH
Ac-His-(D)Phe-Arg-(D)Trp-Gly-$NH_2$
Ac-Nle-Gln-His-(D)Phe-Arg-(D)Trp-Gly-OH
Ac-Nle-Gln-His-(D)Phe-Arg-(D)Trp-Gly-$OC_2H_5$
Ac-Nle-Gln-His-(D)Phe-Arg-(D)Trp-Gly-NH-$NH_2$
Ac-Nle-Asn-His-(D)Phe-Arg-(D)Trp-Gly-$NH_2$
Ac-Nle-Asn-His-(D)Phe-Arg-(D)Trp-Gly-OH
Ac-Nle-Gln-His-(D)Phe-Arg-(D)Trp-Gly-$NHCH_2CH_2Ph$
Ac-Nle-Gln-His-(D)Phe-Arg-(D)Trp-Gly-$NHCH_2Ph$

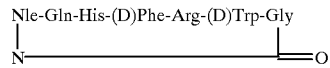

Gln-His-(D)Phe-Arg-(D)Trp-Gly-$NH_2$
Ac-Gln-His-(D)Phe-Arg-(D)Trp-Gly-$NH_2$
Ac-Nle-Gln-His-(D)Phe-Arg-(D)Trp-$NH_2$
Ac-His-(D)Phe-Arg-(D)Trp($CH_2$)-(NAc)Gly-$NH_2$
His-(D)Phe-Arg-(D)Trp($CH_2$)-(NAc)Gly

Amino acids are indicated by their commonly known three-letter code. Nle is the three-letter code for norleucine. The prefix (D)-designates an amino acid having the D-configuration, as opposed to the naturally occurring L-configuration. Where no specific configuration is indicated, a skilled artisan would understand the amino acid to be an L-amino acid. Finally, Ph indicates a phenyl group ($C_6H_5$).

A skilled artisan would know that the choice of amino acids or amino acid analogs incorporated into the compound will depend in part on the specific physical, chemical or biological characteristics required of the compound. Such characteristics can be determined by the route of administration and the desired location of action.

Selective modification of the reactive groups also can impart desirable characteristics to the compound. During synthesis, compounds can be manipulated while still attached to a resin to obtain N-terminal modified compounds such as an acetylated peptide or can be removed from the resin using hydrogen fluoride or an equivalent cleaving reagent and then modified. Compounds synthesized containing the C-terminal carboxyl group (Wang resin) can be modified after cleavage from the resin or prior to solution phase synthesis.

Methods for modifying the N-terminus or C-terminus of a peptide are well known in the art and include methods for acetylating the N-terminus or amidating the C-terminus. Similarly, methods for modifying side chains of the amino acids or amino acid analogs are well known to those skilled in the art of peptide synthesis. The choice of modifications made to the reactive groups present on the peptide will be determined by the desired characteristics.

Cyclic peptides can also be compounds useful in the method of the invention. A cyclic peptide can be obtained by inducing the formation of a covalent bond between the amino group at the N-terminus of the peptide and the carboxyl group at the C-terminus. For example, the peptide cyclo(His-(D)Phe-Arg-(D)Trp) can be produced by forming a covalent bond between His and (D)Trp. A cyclic peptide can also be obtained by forming a covalent bond between a terminal reactive group and a reactive amino acid side chain or between two reactive amino acid side chains. One skilled in the art would know that the choice of a particular cyclic peptide is determined by the reactive groups present on the peptide as well as the desired characteristic of the peptide. For example, a cyclic peptide may provide a compound with increased stability in vivo.

The compound can also be administered to the subject by any number of routes known in the art. These routes include injection parenterally, such as intravenously (i.v.) for systemic administration, intramuscularly, subcutaneously, intraorbitally, intracapsularly, intraperitoneally (i.p.), intracisternally, intra-articularly. Other routes include orally, intravaginally, rectally, or oral or topical intubation, which can include direct application of an ointment or powder, or using a nasal spray or inhalant, which may include a propellant.

The compound can be administered through the skin by passive absorption such as a skin patch or facilitated absorption such as transdermal iontophoresis. Particular routes include transdermal delivery by passage through the skin into the blood stream and transmucosal delivery through mucosal tissue. Another route is transurethral or intraurethral, where the compound contacts and passes through the wall of the urethra and enters the blood stream.

The compound can also be incorporated into liposomes, microspheres or other polymer matrices (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

An "effective dose" of the compound herein means an amount of the composition that is sufficient to therapeutically alleviate a sexual dysfunction in a subject or to prevent or delay onset or recurrence of the dysfunction.

The amount of a therapeutically effective dose depends on a variety of factors, including the particular characteristics of the compound, the type and severity of the sexual dysfunction and the patient's medical condition. Based on such factors, a skilled physician can readily determine a therapeutically effective dose of the compound, which can be about 0.01 to 100 mg/kg body weight per administration. For example, the compound can be administered at 0.0001, 0.0005, 0.001, 0.005, 0.01, 0.05, 0.1, 0.5, 1, 5, 10, 50 or 100 mg/kg body weight.

The total amount of compound can be administered as a single dose as a bolus or by infusion over a relatively short period of time, or can be administered in multiple doses administered over a more prolonged period of time. One skilled in the art would know that the amount of a compound depends on many factors including the age and general health of the subject as well as the route of administration and the number of treatments to be administered. In view of these factors, the skilled artisan would adjust the particular dose to obtain an effective dose for treating sexual dysfunction.

A compound can be administered to a subject as a pharmaceutical composition comprising the compound and a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that stabilize the compound or increase its absorption. Such physiologically acceptable compounds include carbohydrates such as glucose, sucrose or dextrans; antioxidants, such as ascorbic acid or glutathione; chelating agents; low molecular weight proteins or other stabilizers or excipients. One skilled in the art would know that the choice of a pharmaceutically acceptable carrier depends on the route of administration of the compound and on its particular physico-chemical characteristics.

The compounds described above can interact with melanocortin (MC) receptors to affect their activity. Five distinct MC receptors have been cloned and are known to mediate a variety of physiological effects. For example, MC-1 is involved in pain and inflammation. The MC receptors have also been implicated in the regulation of weight control, adrenal gland function such as production of the glucocorticoid cortisol and aldosterone, control of melanocyte growth and pigment production, thermoregulation, immunomodulation and analgesia.

The diversity of physiological responses to MC receptor signaling can be used to alter or regulate a physiological pathway that mediates or moderates a pathological condition or disease. Thus, the binding of an MC receptor ligand to an MC receptor can be used to modulate physiological responses.

The recent elucidation of the role of various MC receptors in particular physiological pathways supports the use of ligands that activate specific MC receptors to modulate a physiological effect associated with a given condition or disease. The A-MSH analog MELANOTAN-II, which is an MC receptor ligand, has been shown to cause penile erections in human subjects in pilot phase I clinical studies (Dorr et al., *Life Sciences* 58:1777–1784 (1996)). Due to the lack of ligands specific for particular MC receptors, however, the specific receptor associated with erectogenesis has been uncertain (Vergoni et al., *Eur. J. Pharmacol.* 362:95–101 (1998)).

The present invention discloses that the receptor MC-3 is specifically associated with sexual dysfunction. As discussed in Example VI, this is demonstrated using a compound that acts as an MC-3-specific antagonist. Therefore, ligands for MC-3 that can alter the activity of an MC-3 receptor can be useful for treating sexual dysfunction and other conditions or conditions associated with MC-3 such as inflammation.

Other MC-3-associated conditions that can be treated with the MC-3 receptor ligands include disuse deconditioning; organ damage such as organ transplantation or ischemic injury; adverse reactions associated with cancer chemotherapy; diseases such as atherosclerosis that are mediated by free radicals and nitric oxide action; bacterial endotoxic sepsis and related shock; adult respiratory distress syndrome; and autoimmune or other patho-immunogenic diseases or reactions such as allergic reactions or anaphylaxis, rheumatoid arthritis, inflammatory bowel disease, ulcerative colitis, glomerulonephritis, systemic lupus erythematosus, transplant atherosclerosis and parasitic mediated immune dysfunctions such as Chagas's Disease.

Accordingly, the present invention provides a method for selecting an MC-3 ligand by initially contacting a compound with an MC-3 receptor. It is then determined whether the compound modulates the activity of the receptor. The compound is selected if the compound modulates the activity of the receptor.

A variety of assays can be used to measure activity modulation by MC-3 receptor ligands. Because MC receptors are G-protein-coupled receptors that activate adenylate cyclase and produce cAMP in response to binding of ligands, a cAMP assay can be useful for determining whether a compound can modulate an MC-3 receptor's activity. Such as assay is described in Example IV.

A particular MC-3 ligand can modulate the receptor's activity as an agonist. The term "agonist" means herein a ligand that increases or otherwise stimulates the activity of the MC-3 receptor. An increase in activity can be detected in a cAMP assay by elevation in cAMP compared to a negative control. The potency of the agonist can be represented in terms of $EC_{50}$, which is the concentration of ligand necessary to achieve 50% of the maximum increase by that agonist in an assay. Thus, an MC-3 agonist can have an $EC_5$ less than 1 µM. More potent agonists can have an $EC_{50}$ less than 500, 200, 100 or 50 nM. HP-228, which is a powerful MC-3 agonist, can be used as a positive control for the assay. Thus, the MC-3 ligand can also be measured in comparison with HP-228, having at least 25%, 50%, 75% or even 100% of the MC-3 stimulatory effect of HP-228 in the assay.

A particular MC-3 ligand can also act as an antagonist. The term "antagonist" herein means a ligand that binds to an MC-3 receptor, resulting in any decrease in the receptor's activity. The decrease can be determined in a cAMP assay by detecting a reduction in the stimulatory effect of HP-228. The potency of the antagonist can also be represented in terms of $EC_5$, where $EC_{50}$ is the concentration of ligand necessary to achieve 50% of the maximum decrease by that antagonist in an assay. An example of an antagonist is TRG 2411 #203, as described in Example II.A.

An MC-3 antagonist can be particularly useful for decreasing an MC-3-associated condition. For example, where penile erections are mediated by MC-3, decreasing the MC-3 activity using an MC-3 antagonist can be useful for treating priapism or otherwise reducing the ability of a subject to maintain an erection.

While a ligand that binds MC-3 and modulates MC-3 activity is useful, the same ligand may also be able to bind other MC receptors. If so, the ligand may also modulate the activity of those other receptors to some degree. While the presence of non-MC-3 activity may not necessarily be detectable or interfere with the intended effect of an MC-3 ligand, it can be desirable to select an MC-3 ligand so that such non-MC-3 activity is minimized. Thus, a particularly useful ligand can also show preferential or selective activity for MC-3 compared to other melanocortin receptors.

Thus, the selection method described above can further comprise the step of determining whether the ligand is MC-3-preferring compared to a second melanocortin receptor. The compound can then be selected only if the compound is both an MC-3 ligand and MC-3-preferring. The term "second melanocortin receptor" as used herein can be any one or combination of MC-1, MC-2, MC-4, MC-5, or any other known melanocortin receptor other than MC-3.

A ligand can be "MC-3-preferring" in two ways, as illustrated in Example V. First, an agonist can be MC-3-preferring if the ligand has a lower $EC_{50}$ for MC-3 than for the second MC. For example, the ligand's $EC_5$ for MC-3 can be less than 5%, 10%, 20%, 50% or 100% of the ligand's $EC_{50}$ for the second MC, as measured by a cAMP assay. Similarly, an MC-3-preferring antagonist can have a lower $EC_{50}$ for MC-3 than for the second MC.

A ligand agonist or antagonist can also be MC-3-preferring by binding more tightly to MC-3 than to another melanocortin receptor. For example, the ability of a ligand compound to compete for binding of a known MC receptor ligand can be used to assess the affinity and specificity of the compound for one or more MC receptors. An example of such a competition assay is presented in Example III.

Any MC receptor ligand can be used so long as the competing ligand can be labeled with a detectable moiety. The detectable moiety can be a radiolabel, fluorescent label or chromophore, or any detectable functional moiety so long as the MC receptor ligand exhibits specific MC receptor binding. A particularly useful detectable MC receptor ligand for identifying and characterizing other MC receptor ligands is [125]I-HP 467, which has the amino acid sequence Ac-Nle-Gln-His-(para-[125]iodo-(D)Phe)-Arg-(D)Trp)-Gly-$NH_2$.

The binding affinity of a ligand for an MC receptor can be expressed as an $IC_{50}$ value, which is the concentration giving 50% inhibition of binding of [125]I-HP 467. Thus, an MC-3-preferring ligand can have a lower $IC_{50}$ for MC-3 than for the second MC. For example, the ligand's $IC_{50}$ for MC-3 can be less than 5%, 10%, 20%, 50% or 100% of the ligand's $IC_{50}$ for the second MC.

While an MC-3 ligand can have similar $EC_{50}$ and $IC_{50}$ profiles across several MC receptors, the profiles can also be different due to different receptor sources used in the assays. For example $EC_{50}$ profiles may be determined using non-human MC receptors such as mouse or rat, while $IC_{50}$ profiles are determined using human MC receptors, or vice versa. Thus, both activity and binding preferences, as manifested by $EC_{50}$ and $IC_{50}$ profiles, can be separately useful for determining the MC-3 preference of a ligand. In addition, MC preferences may also differ when the profiles are determined in vivo or in vitro.

The invention also provides a method for screening a library of compounds for MC-3 ligands by selecting the compounds from the library for MC-3 modulating activity, as described above. The library can have at least 50, 100, 200, 500 or even 1000 compounds. Such libraries have been described extensively in the literature and can be generated by combinatorial or other methods or can be obtained commercially.

Compounds obtained by screening such libraries may not be immediately administerable to a subject and may require an additional pharmaceutically acceptable carrier, as described above. In particular, the ligand may not be readily soluble or be able to reach the intended target area in effective concentrations. For example, the ligand may not readily cross the blood-brain barrier upon administration. One skilled in the art will recognize that numerous methods are known in the art to solubilize and administer initially insoluble compounds, such as dissolving the compound in 20% DMSO or 20% CDEX dextran (w/v). As also discussed above, these solubility and other considerations will be recognized by the skilled artisan when determining the effective dose of the compound when used to treat an MC-3-associated condition.

The invention further provides a method for treating an MC-3-associated condition in a subject. The term "MC-3-associated condition" includes any condition or condition mediated by MC-3 or can be affected by binding an MC-3 ligand. Such conditions include inflammation and sexual dysfunction. The method comprises administering to the subject an effective dose of a pharmaceutical composition, which comprises a pharmaceutically acceptable carrier and a compound obtained by screening a compound library, as described above.

Useful compounds obtained from screening libraries include benzamidazoles, which have the generic starting structure

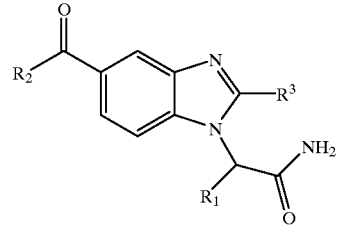

The $R_1$, $R_2$ and $R_3$ positions can then be derivatized with compounds having functional groups using standard organic chemistry techniques. The variable $R_1$ can be derivatized with an amino acid. The variable $R_2$ can be derivatized with a primary or secondary amine. The variable $R_3$ can be derivatized with an aldehyde.

Particular compounds can be selected by further defining one or more of the individual variables in the generic formula above. Thus, $R_1$ can be derivatized with arginine; $R_2$ can be derivatized with phenethylbenzylamine or 2-phenyl-phenethylamine; and $R_3$ can be derivatized with 4-t-butylbenzaldehyde, 4-i-propylbenzaldehyde or 4-butoxybenzaldehyde.

Specific benzamidazole compounds are designated Compounds A to E as follows. In Compound A $R_1$ is derivatized with arginine, $R_2$ is derivatized with phenethylbenzylamine and $R_3$ is derivatized with 4-t-butylbenzaldehyde:

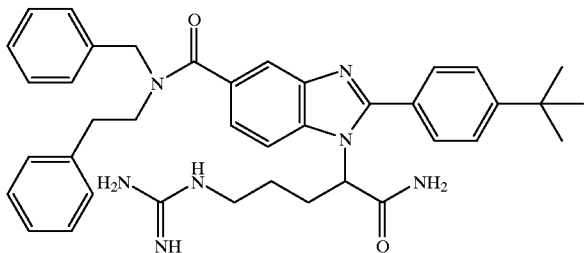

In Compound B, $R_1$ is derivatized with arginine, $R_2$ is derivatized with 2-phenyl-phenethylamine and $R_3$ is derivatized with 4-butoxybenzaldehyde:

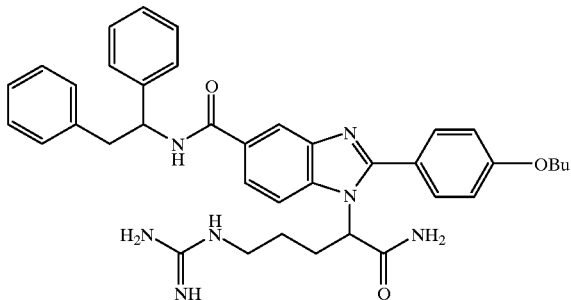

In Compound C, $R_1$ is derivatized with arginine, $R_2$ is derivatized with 2-phenyl-phenethylamine and $R_3$ is derivatized with 4-i-propylbenzaldehyde:

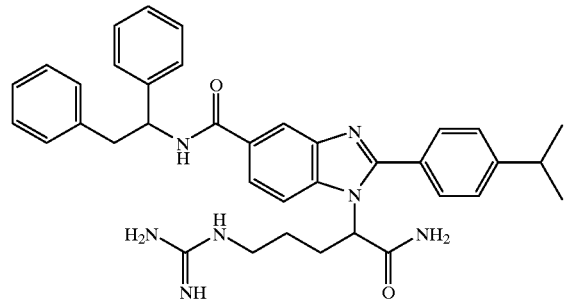

In Compound D, $R_1$ is derivatized with arginine, $R_2$ is derivatized with phenethylbenzylamine and $R_3$ is derivatized with 4-i-propylbenzaldehyde:

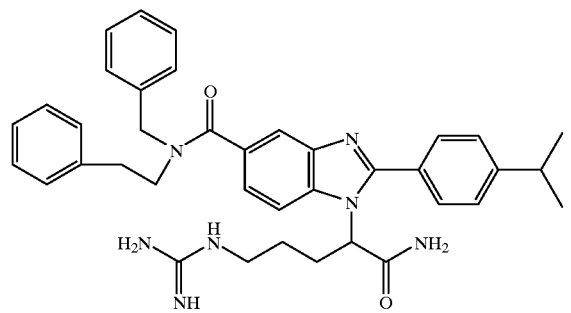

In Compound E, $R_1$ is derivatized with arginine, $R_2$ is derivatized with 1,2-diphenolethylamine and $R_3$ is derivatized with 4-t-butylbenzaldehyde:

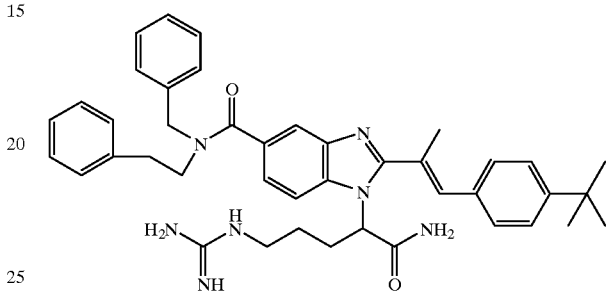

The following examples are intended to illustrate but not limit the invention.

EXAMPLE I

Synthesis of Compounds

A. Synthesis of HP-228

HP-228 was synthesized essentially as described in U.S. Pat. No. 5,420,109.

Briefly, 100 mg MBHA resin containing a t-Boc Gly derivative was added to a reaction vessel suitable for solid phase peptide synthesis (Houghten, Proc. Natl. Acad. Sci. USA 82:5131 (1985)). The following conditions were used for peptide synthesis: coupling was performed in 6-fold excess in N,N-dimethylformamide (DMF) with 0.2 M N-hydroxybenzotriazole(HOBt) and 0.2 M N,N-diisopropylcarbodiimide (DIC) for 90 minutes; activation was performed with 5% diisopropylethylamine (DIEA) in methylene chloride (DCM) for three washes of 2 min; deprotection was performed with 55% trifluoroacetic acid (TFA) for 30 min; washes were performed with DCM and isopropanol; the ninhydrin test was run after washing with DMF, DCM and methanol; acetylation was performed with acetylimidazole in 40-fold excess DCM for 4 hr; and cleavage was performed with hydrofluoric acid (HF) and anisole for 90 min.

Peptide synthesis was carried out with the sequential steps of activation, coupling of amino acid, ninhydrin test, deprotection and washing, and the steps were repeated for addition of a new amino acid at each cycle. The amino acids were coupled in the order D-Trp, L-Arg, (D)Phe, L-His, L-Gln and L-Nle. The peptide was acetylated and the DNP protecting group was removed from is using 2.5% thiophenol in DMF followed by removal of formyl protecting groups in 25% HF in dimethylsulfide. The peptide was cleaved from the resin and processed as described previously (U.S. Pat. No. 5,420,109). The resulting peptide was approximately 80 to 90% pure.

B. Preparation of HP-467

Compound HP-467 was prepared by iodinating HP-228, described above. The iodinated compound can be radiolabeled or unlabeled.

For iodination, 100 µl 2 N H$_2$SO$_4$ and 400 µl 0.5 M CuSO$_4$ was added to 12 mg Zn powder, and the components were allowed to react with periodic mixing for 30 to 45 min, with venting, until bubbling stopped. The grains were washed twice with water. For unlabeled peptide, 7.12 µl of 0.67 mM NaI (0.0047 µmol) was added to the reaction vial. For radiolabeled peptide, 0.0047 µmol of Na$^{125}$I was added to the reaction vial. Approximately ⅛ of the copper grains were added to the vial, and the vial was vortexed for 1 minute. The reaction was carried out vented at room temperature for 3 hr with periodic mixing.

Samples were analyzed on a Vydac 218TP54 C-18 column and were monitored at 214 nm. Buffer A was 0.05% TFA in water, and Buffer B was 0.05% TFA in acetonitrile. Samples were resolved using a 2% per minute gradient from 5 to 55% Buffer B in 25 min.

Using this method, $^{125}$I-HP 467 was routinely labeled to a specific activity of 2000 Ci/mmol. These results demonstrate that HP-467 can be iodinated to generate unlabeled iodo-peptide or high specific activity radiolabeled iodo-peptide.

EXAMPLE II

Induction of Erections Upon Administration of HP-228

A. Induction of Erections in Rats

Adult male rats were housed 2 to 3 per cage and were acclimated to the standard vivarium light cycle (12 hr. light, 12 hr. dark), rat chow and water for a least a week prior to testing. All experiments were performed between 9 a.m. and noon and rats were placed in cylindrical, clear plexiglass chambers during the 60 minute observation period. Mirrors were positioned below and to the sides of the chambers to improve viewing.

Observations began 10 minutes after an intraperitoneal injection of either saline or compound. An observer counted the number of grooming motions, stretches, yawns and spontaneously occurring penile erections not elicited by genital grooming, and then recorded them every 5 minutes for a total of 60 minutes. The observer was unaware of the treatment and animals were tested once, with n =6 in each group. Values in the figures represent the group mean. HP-228 was used as a positive control for penile erections. Significant differences between groups were determined by an overall analysis of variance and the Student Neunmann-Keuls post hoc test was used to identify individual differences between groups (p <0.05).

Upon observation, an average of 4.8 erections were observed per hour, compared to 0.2 for vehicle (PBS), thus demonstrating that HP-228 can induce erections in rats. Injection with HP-228 with antagonist TRG 2411 #203 reduced the average number of erections observed to 2.7.

B. Dose-response Curve in Rats

This example describes a dose-response correlation for using HP-228 to induce erections in rats.

Adult male Sprague-Dawley rats weighing 220 to 250 g or adult male Balb/c (Harlan Laboratories; Indianapolis Ind.) were anesthetized and then injected intracerebroventricularly (ICV) with 5 to 10 microliters (1 ml/kg body weight) HP-228 solution or PBS as a negative control. Concentrations of HP-228 were 0.45, 0.9, 1.8, 3.6 and 7.2 mg/kg (n =4 to 6 animals). The animals were allowed 10 minutes to recover from the anesthesia before observation. The animals were then observed for 60 to 90 minutes for penile erections not induced by grooming. Yawning, stretching, grooming behaviors were also recorded.

| mg/kg HP-228 | avg. erections observed/hour |
|---|---|
| 0.0 (control) | 0.25 |
| 0.45 | 2.80 |
| 0.9 | 2.60 |
| 1.8 | 3.67 |
| 3.6 | 7.00 |
| 7.2 | 5.75 |

These results demonstrate a dose-response effect by HP-228 for inducing erections in rats.

C. Dose-response Curve in Mice

This example describes a dose-response correlation for using HP-228 to induce erections in mice (n=3 to 5). Age-matched C57/B16 mice (Harlan Laboratories; Indianapolis IN) weighing 20 to 25 g were injected (100 µl/mouse) essentially as described above and observed.

| µg/mouse HP-228 | avg. erections observed/hour |
|---|---|
| 0 (control) | 0.33 |
| 25 | 3.00 |
| 50 | 6.67 |
| 100 | 5.33 |
| 250 | 3.00 |

These results demonstrate that HP-228 is also erectogenic in mice.

EXAMPLE III

Melanocortin Receptor Assay

This example describes methods for assaying ligand binding to MC receptors.

All cell culture media and reagents were obtained from GibcoBRL (Gaithersburg Md.), except for COSMIC CALF SERUM (HyClone; Logan Utah). HEK 293 cell lines were transfected with human MC receptors hMCR-1, hMCR-3 and hMCR-4 (Gantz et al., *Biochem. Biophys. Res. Comm.* 200:1214–1220 (1994); Gantz et al., *J. Biol. Chem.* 268:8246–8250 (1993); Gantz et al. *J. Biol. Chem.* 268:15174–15179 (1993); Haskell-Leuvano et al., *Biochem. Biophys. Res. Comm.* 204:1137–1142 (1994)). Vectors for constructing an hMCR-5-expressing cell line were obtained and a line of HEK 293 cells expressing hMCR-5 was constructed (Gantz, supra, 1994). Receptor hMCR-5 has been described previously (Franberg et al., *Biochem. Biophys. Res. Commun.* 236:489–492 (1997); Chowdhary et al., *Cytogenet. Cell Genet.* 68:1–2 (1995); Chowdhary et al., *Cytogenet. Cell Genet.* 68:79–81 (1995)). HEK 293 cells were maintained in DMEM, 25 mM HEPES, 2 mM glutamine, non-essential amino acids, vitamins, sodium pyruvate, 10% COSMIC CALF SERUM, 100 units/ml penicillin, 100 pg/ml streptomycin and 0.2 mg/ml G418 to maintain selection.

Before assaying, cells were washed once with phosphate buffered saline (PBS without Ca$^{2+}$ and Mg$^{2+}$) and stripped from the flasks using 0.25% trypsin and 0.5 mM EDTA. Cells were suspended in PBS, 10% COSMIC CALF SERUM and 1 mM CaCl$_2$. Cell suspensions were prepared at a density of $2 \times 10^4$ cells/ml for HEK 293 cells expressing hMCR-3, hMCR-4 or hMCR-5, and $1 \times 10^5$ cells/ml for HEK 293 cells expressing hMCR-1. Suspensions were placed in a water bath and allowed to warm to 37° C for 1 hr.

Binding assays were performed in a total volume of 250 μl for HEK 293 cells. Control and test compounds were dissolved in distilled water. Custom labeled ligand $^{125}$I-HP 467 (50,000 dpm, 2000 Ci/mmol) (Amersham; Arlington Heights Ill.) was prepared in 50 mM Tris, pH 7.4, 2 mg/ml BSA, 10 mM $CaCl_2$, 5 mM $MgCl_2$, 2 mM EDTA and added to each tube. To each tube was added $4 \times 10^3$ HEK 293 cells expressing hMCR-3, hMCR-4 or hMCR-5, or $2 \times 10^4$ cells expressing hMCR-1. Assays were incubated for 2.5 hours at 37° C.

GF/B filter plates were prepared by soaking for at least one hour in 5 mg/ml BSA and 10 mM $CaCl_2$. Assays were filtered using a Brandel 96-well cell harvester (Brandel Inc.; Gaithersburg Md.). The filters were washed four times with cold 50 mM Tris, pH 7.4; the filter plates were dehydrated for 2 hr; and 35 μl of MICROSCINT was added to each well. Filter plates were counted using a Packard Topcount (Packard Instrument Co.; Meriden Conn.) and data analyzed using GraphPad PRISM v2.0 (GraphPad Software Inc.; San Diego Calif.) and Microsoft EXCEL v5.0a (Microsoft Corp.; Redmond Wash.).

To assay compounds, binding assays were performed in duplicate in a 96-well format. HP 467 was prepared in 50 mM Tris, pH 7.4, and $^{125}$I-HP 467 was diluted to give 100,000 dpm per 50 μl. A compound was added to the well in 25 μl aliquots. A 25 μl aliquot of $^{125}$I-HP 467 was added to each well. A 0.2 ml aliquot of suspended cells was added to each well to give the cell numbers indicated above, and the cells were incubated at 37° C. for 2.5 hours. Cells were harvested on GF/B filter plates as described above and counted.

EXAMPLE IV cAMP Assay for Melanocortin Receptors

This example describes methods for assaying cAMP production from G-protein-coupled MC receptors.

HEK 293 cells expressing MCR-1, MCR-3, MCR-4 and MCR-5 were used. Cells were plated at 20,000 cells per well in a 96-well plate coated with collagen. The next day, cells were pretreated with 75 μl of 0.4 mM 3-isobutyl-1-methylxanthine (IBMX) in low serum medium containing DMEM, 25 mM HEPES, non-essential amino acids, vitamins, 100 units/ml penicillin, 100 μg/ml streptomycin and 0.1% COSMIC CALF SERUM. IBMX is an inhibitor of cAMP phosphodiesterase. The pretreatment was carried out for 10 minutes at 37° C.

Following pretreatment, 25 μl of diluted compound was added to the wells and cells were incubated for 15 min at 37° C. Cells were lysed by adding 25 μl saponin lysis buffer and incubating 2 to 5 minutes. Plates were covered and stored at −20° C.

The cAMP concentration was determined by ELISA. Briefly, 96 well ELISA plates were coated with goat anti-cAMP antibody in PBS for 12 to 72 hr at 4° C. 50 μl of sample was mixed with 50 μl of cAMP ELISA buffer containing 1% bovine serum albumin, 10% heat inactivated donor horse serum, 1% normal mouse serum and 0.05% TWEEN-20 in PBS, and the diluted sample was added to the coated ELISA plate. Standards of known concentrations of cAMP were added to separate wells. Then, cAMP-conjugated horseradish peroxidase (cAMP-HRP) was added to each well at 25 μl of 16 ng/ml. The plates were incubated for 3 hr at room temperature. Plates were washed and the binding of cAMP-HRP was detected with 3,3',5,5'-tetramethylbenzidine (TMB) and hydrogen peroxide using standard immunoassay procedures.

EXAMPLE V

Melanocortin Receptor Binding Profile of Compounds

Various compounds were tested for in vitro activity and binding to melanocortin receptors. MC-3 stimulatory effect is also described in terms of percentage of stimulation obtained by adding HP-228. The $EC_{50}$ values are the concentration of ligand necessary to achieve 50% of the maximum increase by that ligand in an assay. The $IC_{50}$ values are the concentration giving 50% inhibition of binding of $^{125}$I-HP 467.

| | | $EC_{50}$ (μM) values | | |
|---|---|---|---|---|
| Compound | % of HP-228 | MC-3 | MC-1 | MC-4 |
| A | 89% | 7.65 | 0.47 | |
| B | 115% | 1.33 | | 12 |
| C | 92% | 1.4 | | 10.6 |
| D | 140% | 1.7 | | 2.8 |
| E | 59% | 6.7 | 0.43 | 19.9 |

These results show that the Compounds A to E can act as MC-3 agonists, often exceeding the stimulatory activity of HP-228 in comparable assays. Moreover, Compounds B to E each have a greater stimulatory effect on MC-3 than another MC receptor, thus demonstrating MC-3-preferring activity.

Compounds E and F (structures not shown) were tested for competitive binding to MC-3, MC-1, MC-4 and MC-5.

| | $IC_{50}$ (μM) values | | | |
|---|---|---|---|---|
| Compound | MC-3 | MC-1 | MC-4 | MC-5 |
| F | 2.664 | 1.668 | 2.849 | 0.343 |
| G | 4.015 | 1.175 | 5.808 | 0.325 |
| H | 1.455 | 0.645 | 4.682 | 0.269 |
| I | 0.405 | 3.385 | 2.164 | 0.172 |
| J | 10.863 | 15.496 | 20.160 | 28.049 |

These results demonstrate that compounds such as Compound J can have stronger binding to MC-3 compared to other melanocortin receptors. In addition, although Compound I does binds MC-5, it binds MC-3 more tightly than MC-1 or MC-4 and is therefore considered MC-3-preferring.

EXAMPLE V

Association of MC-3 With Erectile Response

This example shows that erectogenesis is associated with MC-3.

Sprague-Dawley rats (n=5) received 1.8 mg/kg HP-228 or PBS via IP. The rats also received via ICV a dose of PBS or MC-3-specific antagonist at 10 μg/5 μl. After administration, the rats were observed as described above.

In the negative control rats, receiving only PBS, 0.3 erections per hour were observed. In the positive control rats, receiving HP-228 but no MC-3 antagonist, 3.8 erections per hour were observed. In rats receiving HP-228 and the MC-3-specific antagonist, the number of erections observed decreased to 0.8 per hour, demonstrating that the HP-228-induced erections were antagonized by the MC-3-specific antagonist, thereby identifying MC-3 as the MC receptor associated with erectogenesis. No erections were observed in the rats receiving the MC-3-specific antagonist and no HP-228. The MC-3-specific antagonist is also known to have MC-4 agonist properties, which were reflected by significantly reduced food consumption.

Although the invention has been illustrated by the examples above, it should be understood that various modifications can be made without departing from the spirit of the invention. Accordingly, the invention is limited only by the following claims.

We claim:

1. A method for treating erectile dysfunction in a male subject, comprising the step of administering to the subject an effective dose of the compound $X_1$–$X_2$-(D)Phe-Arg-(D)Trp-$X_3$ wherein

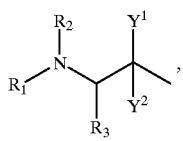

$COCH_3$, H or absent;

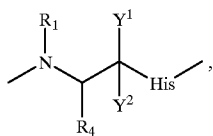

His, $COCH_3$ or H; and

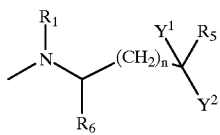

or $R_5$; wherein $R_1$ is H, $COCH_3$, $C_2H_5$, $CH_2Ph$, COPh, COO-t-butyl, $COOCH_2Ph$, $CH_2CO$-(polyethylene glycol) or A;

$R_2$ is H, $COCH_3$, $C_2H_5$ or $CH_2Ph$;

$R_3$ is a linear alkyl group having 1 to 6 carbon atoms or a branched or cyclic alkyl group having 3 to 6 carbon atoms;

$R_4$ is $(CH_2)_m$—$CONH_2$, $(CH_2)_m$—$CONHR_1$ or $(CH_2)_m$—CONHA;

$R_5$ is OH, $OR_3$, $NH_2$, SH, $NHCH_3$, $NHCH_2Ph$ or A;

$R_6$ is H or $R_3$;

$R_7$ is H, $COCH_3$, $C_2H_5$, $CH_2Ph$, COPh, COO-t-butyl, $COOCH_2Ph$ or $CH_2CO$-(polyethylene glycol);

Ph is $C_6H_5$; m is 1, 2 or 3; n is 0, 1, 2 or 3; $Y^1$ and $Y^2$ are independently hydrogen atoms, or are taken together to form a carbonyl or thiocarbonyl; and A is

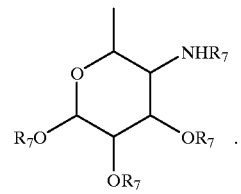

2. The method of claim 1, wherein $X_1$ is selected from the group consisting of norleucine and Ac-norleucine.

3. The method of claim 1, wherein $X_1$ is selected from the group consisting of norvaline, Ac-norvaline, leucine, Ac-leucine, isoleucine and Ac-isoleucine.

4. The method of claim 1, wherein $X_2$ is selected from the group consisting of Gln-His and His.

5. The method of claim 1, wherein $X_3$ is selected from the group consisting of Gly and Gly-$NH_2$.

6. The method of claim 1, wherein $R_1$ is selected from the group consisting of H, $C_2H_5$ and $CH_2Ph$.

7. The method of claim 1, wherein $R_1$ and $R_2$ are independently selected from the group consisting of $COCH_3$ and H.

8. The method of claim 1, wherein $R_5$ is $NH_2$.

9. The method of claim 1, wherein $R_5$ is covalently bound to $X_1$, forming a cyclic peptide.

10. The method of claim 1, wherein the compound HP-228, having the structure Ac-Nle-Gln-His-(D)Phe-Arg-(D)Trp-Gly-$NH_2$.

11. The method of claim 1, wherein the (D)Phe is iodinated in the para position.

12. The method of claim 11, wherein the compound is Ac-Nle-Gln-His-(para-iodo-(D)Phe)-Arg-(D)Trp-Gly-$NH_2$.

13. The method of claim 1, wherein the compound is selected from group consisting of (D)Phe-Arg-(D)Trp, Ac-(D)Phe-Arg-(D)Trp, (D)Phe-Arg-(D)Trp-$NH_2$ and Ac-(D)Phe-Arg-(D)Trp-$NH_2$.

14. The method of claim 1, wherein the compound is selected from group consisting of (cyclohexyl)Gly-Gln-His-(D)Phe-Arg-(D)Trp-Gly, Ac-(cyclohexyl)Gly-Gln-His-(D)Phe-Arg-(D)Trp-Gly-$NH_2$ and cyclo (His-(D)Phe-Arg-(D)Trp).

15. The method of claim 1, wherein the compound is selected from group consisting of Nle-Gln-His-(D)Phe-Arg-(D)Trp-Gly-$NH_2$, His-(D)Phe-Arg-(D)Trp-Gly, His-(D)Phe-Arg-(D)Trp-Gly-$NH_2$, Ac-His-(D)Phe-Arg-(D)Trp-$NH_2$, His-(D)Phe-Arg-(D)Trp-OH, His-(D)Phe-Arg-(D)Trp, His-(D)Phe-Arg-(D)Trp-$NH_2$, Ac-His-(D)Phe-Arg-(D)Trp-OH and Ac-His-(D)Phe-Arg-(D)Trp-Gly-$NH_2$.

16. The method of claim 1, wherein the compound is selected from group consisting of Ac-Nle-Gln-His-(D)Phe-Arg-(D)Trp-Gly-OH, Ac-Nle-Gln-His-(D)Phe-Arg-(D)Trp-Gly-$OC_2H_5$, Ac-Nle-Gln-His-(D)Phe-Arg-(D)Trp-Gly-NH-$NH_2$, Ac-Nle-Asn-His-(D)Phe-Arg-(D)Trp-Gly-$NH_2$, Ac-Nle-Asn-His-(D)Phe-Arg-(D)Trp-Gly-OH,
Ac-Nle-Gln-His-(D)Phe-Arg-(D)Trp-Gly-NHCH$_2$CH$_2$Ph,
Ac-Nle-Gln-His-(D)Phe-Arg-(D)Trp-Gly-NHCH$_2$Ph,

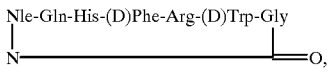

Gln-His-(D)Phe-Arg-(D)Trp-Gly-NH$_2$,
Ac-Gln-His-(D)Phe-Arg-(D)Trp-Gly-NH$_2$,
Ac-Nle-Gln-His-(D)Phe-Arg-(D)Trp-NH$_2$,
Ac-His-(D)Phe-Arg-(D)Trp(CH$_2$)-(NAc)Gly-NH$_2$ and
His-(D)Phe-Arg-(D)Trp(CH$_2$)-(NAc)Gly.

17. A method for treating sexual dysfunction in a female subject, comprising the step of administering to the subject an effective dose of the compound

wherein

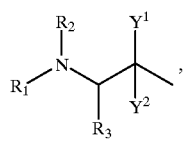

COCH$_3$, H or absent;

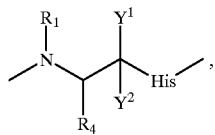

His, COCH$_3$ or H; and

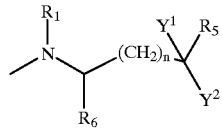

or R$_5$; wherein

R$_1$ is H, COCH$_3$, C$_2$H$_5$, CH$_2$Ph, COPh, COO-t-butyl, COOCH$_2$Ph, CH$_2$CO-(polyethylene glycol) or A;

R$_2$ is H, COCH$_3$, C$_2$H$_5$ or CH$_2$Ph;

R$_3$ is a linear alkyl group having 1 to 6 carbon atoms or a branched or cyclic alkyl group having 3 to 6 carbon atoms;

R$_4$ is (CH$_2$)$_m$—CONH$_2$, (CH$_2$)$_m$—CONHR$_1$ or (CH$_2$)$_m$—CONHA;

R$_5$ is OH, OR$_3$, NH$_2$, SH, NHCH$_3$, NHCH$_2$Ph or A;

R$_6$ is H or R$_3$;

R$_7$ is H, COCH$_3$, C$_2$H$_5$, CH$_2$Ph, COPh, COO-t-butyl, COOCH$_2$Ph or CH$_2$CO-(polyethylene glycol);

Ph is C$_6$H$_5$; m is 1, 2 or 3; n is 0, 1, 2 or 3; Y$^1$ and Y$^2$ are independently hydrogen atoms, or are taken together to form a carbonyl or thiocarbonyl; and A is

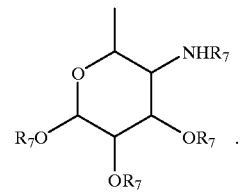

18. The method of claim 17, wherein X$_1$ is selected from the group consisting of norleucine and Ac-norleucine.

19. The method of claim 17, wherein X$_1$ is selected from the group consisting of norvaline, Ac-norvaline, leucine, Ac-leucine, isoleucine and Ac-isoleucine.

20. The method of claim 17, wherein X$_2$ is selected from the group consisting of Gln-His and His.

21. The method of claim 17, wherein X$_3$ is selected from the group consisting of Gly and Gly-NH$_2$.

22. The method of claim 17, wherein R$_1$ is selected from the group consisting of H, C$_2$H$_5$ and CH$_2$Ph.

23. The method of claim 17, wherein R$_1$ and R$_2$ are independently selected from the group consisting of COCH$_3$ and H.

24. The method of claim 17, wherein R$_5$ is NH$_2$.

25. The method of claim 17, wherein R$_5$ is covalently bound to X$_1$, forming a cyclic peptide.

26. The method of claim 17, wherein the compound HP-228, having the structure Ac-Nle-Gln-His-(D)Phe-Arg-(D)Trp-Gly-NH$_2$.

27. The method of claim 17, wherein the (D)Phe is iodinated in the para position.

28. The method of claim 27, wherein the compound is Ac-Nle-Gln-His-(para-iodo-(D)Phe)-Arg-(D)Trp-Gly-NH$_2$.

29. The method of claim 17, wherein the compound is selected from group consisting of
(D)Phe-Arg-(D)Trp,
Ac-(D)Phe-Arg-(D)Trp,
(D)Phe-Arg-(D)Trp-NH$_2$ and
Ac-(D)Phe-Arg-(D)Trp-NH$_2$.

30. The method of claim 17, wherein the compound is selected from group consisting of
(cyclohexyl)Gly-Gln-His-(D)Phe-Arg-(D)Trp-Gly,
Ac-(cyclohexyl)Gly-Gln-His-(D)Phe-Arg-(D)Trp-Gly-NH$_2$ and
cyclo(His-(D)Phe-Arg-(D)Trp).

31. The method of claim 17, wherein the compound is selected from group consisting of
Nle-Gln-His-(D)Phe-Arg-(D)Trp-Gly-NH$_2$,
His-(D)Phe-Arg-(D)Trp-Gly,
His-(D)Phe-Arg-(D)Trp-Gly-NH$_2$,
Ac-His-(D)Phe-Arg-(D)Trp-NH$_2$,
His-(D)Phe-Arg-(D)Trp-OH,
His-(D)Phe-Arg-(D)Trp,
His-(D)Phe-Arg-(D)Trp-NH$_2$,
Ac-His-(D)Phe-Arg-(D)Trp-OH and
Ac-His-(D)Phe-Arg-(D)Trp-Gly-NH$_2$.

32. The method of claim 17, wherein the compound is selected from group consisting of
Ac-Nle-Gln-His-(D)Phe-Arg-(D)Trp-Gly-OH,
Ac-Nle-Gln-His-(D)Phe-Arg-(D)Trp-Gly-OC$_2$H$_5$,
Ac-Nle-Gln-His-(D)Phe-Arg-(D)Trp-Gly-NH-NH$_2$,
Ac-Nle-Asn-His-(D)Phe-Arg-(D)Trp-Gly-NH$_2$, Ac-Nle-Asn-His-(D)Phe-Arg-(D)Trp-Gly-OH,
Ac-Nle-Gln-His-(D)Phe-Arg-(D)Trp-Gly-NHCH$_2$CH$_2$Ph,
Ac-Nle-Gln-His-(D)Phe-Arg-(D)Trp-Gly-NHCH$_2$Ph,
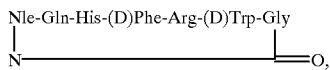
Gln-His-(D)Phe-Arg-(D)Trp-Gly-NH$_2$,
Ac-Gln-His-(D)Phe-Arg-(D)Trp-Gly-NH$_2$,
Ac-Nle-Gln-His-(D)Phe-Arg-(D)Trp-NH$_2$,
Ac-His-(D)Phe-Arg-(D)Trp(CH$_2$)-(NAc)Gly-NH$_2$ and
His-(D)Phe-Arg-(D)Trp(CH$_2$)-(NAc)Gly.
33. The method of claim 17, wherein the dysfunction is sexual arousal disorder.
* * * * *